(12) United States Patent
Costello

(10) Patent No.: US 8,926,694 B2
(45) Date of Patent: Jan. 6, 2015

(54) DUAL VALVE PROSTHESIS FOR TRANSCATHETER VALVE IMPLANTATION

(75) Inventor: Declan Costello, Ballinrobe (IE)

(73) Assignee: Medtronic Vascular Galway Limited, Ballybrit, Galway (IE)

( * ) Notice: Subject to any disclaimer, the term of this patent is extended or adjusted under 35 U.S.C. 154(b) by 246 days.

(21) Appl. No.: 13/432,497

(22) Filed: Mar. 28, 2012

(65) Prior Publication Data

US 2013/0261737 A1 Oct. 3, 2013

(51) Int. Cl.
*A61F 2/24* (2006.01)
(52) U.S. Cl.
USPC .................. 623/2.11; 623/2.18; 623/1.19
(58) Field of Classification Search
USPC ........... 623/1.11, 2.11, 2.15, 2.16, 1.12–1.26; 600/200
See application file for complete search history.

(56) References Cited

U.S. PATENT DOCUMENTS

| 5,957,949 | A | 9/1999 | Leonhardt et al. | |
| 7,530,995 | B2 * | 5/2009 | Quijano et al. | 623/1.24 |
| 2004/0210306 | A1 | 10/2004 | Quijano et al. | |
| 2005/0256566 | A1 * | 11/2005 | Gabbay | 623/2.1 |
| 2006/0241745 | A1 * | 10/2006 | Solem | 623/2.18 |
| 2008/0071362 | A1 | 3/2008 | Tuval et al. | |
| 2008/0183273 | A1 * | 7/2008 | Mesana et al. | 623/1.11 |
| 2009/0248143 | A1 * | 10/2009 | Laham | 623/1.26 |
| 2009/0264991 | A1 * | 10/2009 | Paul et al. | 623/1.35 |
| 2009/0319038 | A1 | 12/2009 | Gurskis et al. | |
| 2011/0106244 | A1 | 5/2011 | Ferrari et al. | |
| 2013/0261739 | A1 | 10/2013 | Kuehn | |
| 2014/0088680 | A1 * | 3/2014 | Costello et al. | 623/1.11 |

FOREIGN PATENT DOCUMENTS

| WO | WO2006111391 | 10/2006 |
| WO | WO2008/091515 | 7/2008 |
| WO | WO2009/092782 | 7/2009 |
| WO | WO2009/129481 | 10/2009 |
| WO | WO2009126362 | 10/2009 |
| WO | WO2012018599 | 2/2012 |
| WO | WO2013059747 | 4/2013 |
| WO | WO2013148019 | 10/2013 |

* cited by examiner

*Primary Examiner* — Dianne Dornbusch
*Assistant Examiner* — Alexander Orkin

(57) ABSTRACT

A dual valve prosthesis having first and second prosthetic valve sections is disclosed. The first prosthetic valve section includes a stent structure with a first prosthetic valve secured therein and the second prosthetic valve section includes an annular frame with a second prosthetic valve secured therein. When the dual valve prosthesis is in an expanded configuration, the annular frame extends from the stent structure such that the first and second prosthetic valves are laterally offset from each other. In a method in accordance herewith, the first and second prosthetic valve sections include prosthetic aortic and mitral valves, respectively, and the dual heart valve prosthesis is configured to replace both the native aortic and mitral valves of the heart in a single transcatheter heart valve implantation procedure.

16 Claims, 4 Drawing Sheets

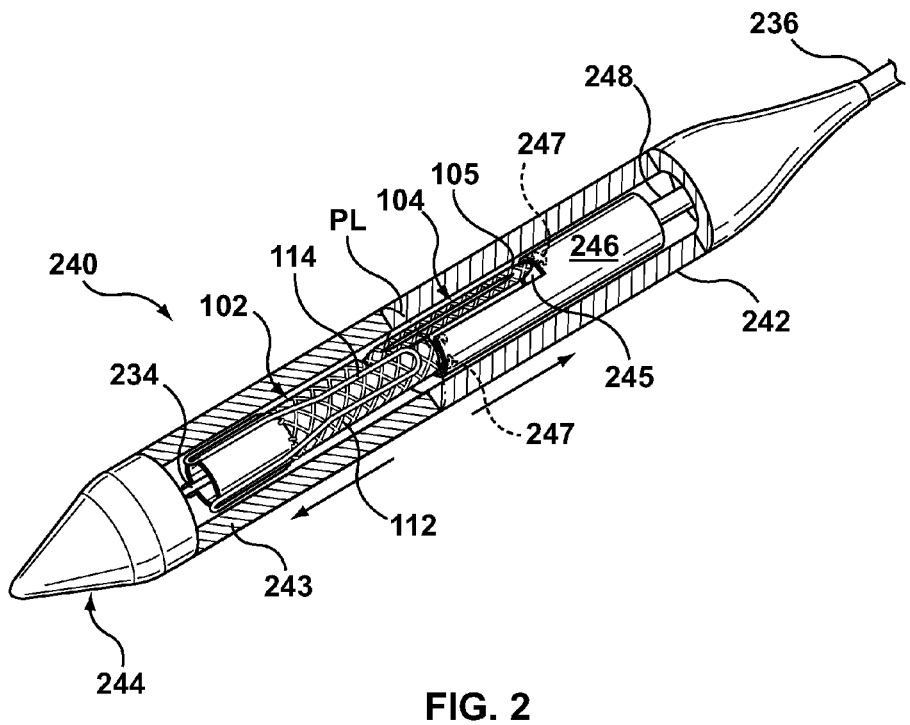
FIG. 2
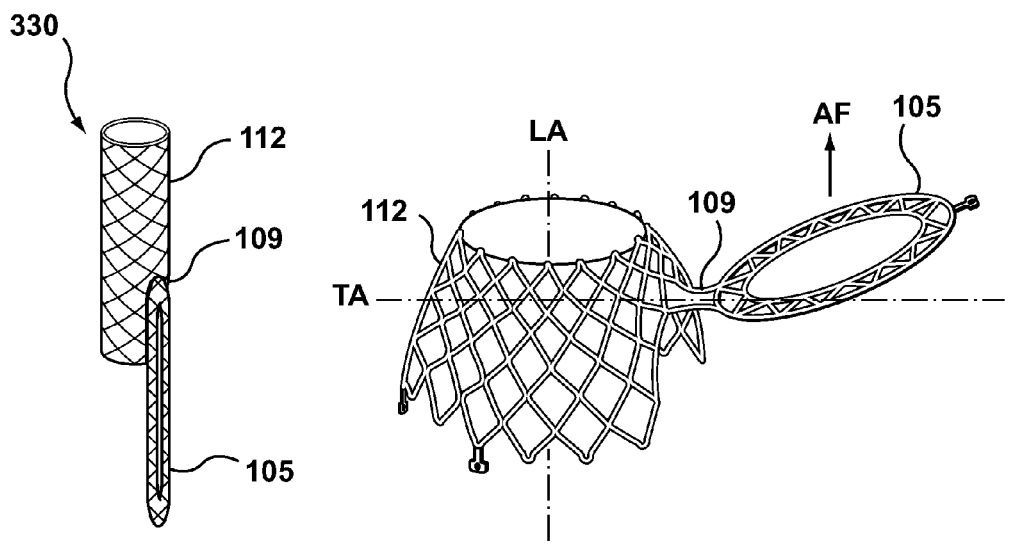
FIG. 3
FIG. 4

DUAL VALVE PROSTHESIS FOR TRANSCATHETER VALVE IMPLANTATION

FIELD OF THE INVENTION

The invention relates generally to a prosthetic valve for replacing a native valve or a previously implanted prosthetic valve in a non-surgical interventional procedure. More particularly, the invention relates to a dual valve prosthesis having a prosthetic aortic valve combined with a prosthetic mitral valve for concurrently replacing the corresponding native valves or previously implanted prosthetic valves in a non-surgical interventional procedure.

BACKGROUND OF THE INVENTION

A wide range of medical treatments are known that utilize "endoluminal prostheses." As used herein, endoluminal prostheses are intended to mean medical devices that are adapted for temporary or permanent implantation within a body lumen, including both naturally occurring and artificially made lumens. Examples of lumens in which endoluminal prostheses may be implanted include, without limitation: arteries, veins, gastrointestinal tract, biliary tract, urethra, trachea, hepatic and cerebral shunts, and fallopian tubes.

Stent prostheses are known for implantation within a body lumen for providing artificial radial support to the wall tissue that defines the body lumen. To provide radial support to a blood vessel, such as one that has been widened by a percutaneous transluminal coronary angioplasty, commonly referred to as "angioplasty," "PTA" or "PTCA", a stent may be implanted in conjunction with the procedure. Under this procedure, the stent may be collapsed to an insertion diameter and inserted into the vasculature at a site remote from the diseased vessel. The stent may then be delivered to the desired treatment site within the affected vessel and deployed, by self-expansion or radial expansion, to its desired diameter for treatment.

Recently, flexible prosthetic valves supported by stent structures that can be delivered percutaneously using a catheter-based delivery system have been developed for heart and venous valve replacement. These prosthetic valves may include either self-expanding or balloon-expandable stent structures with valve leaflets disposed within the interior of the stent structure. The prosthetic valve can be reduced in diameter, by being contained within a sheath component of a delivery catheter or by crimping onto a balloon catheter, and advanced through the venous or arterial vasculature. Once the prosthetic valve is positioned at the treatment site, for instance within an incompetent native or previously implanted prosthetic valve, the stent structure may be expanded to hold the prosthetic valve firmly in place. One embodiment of a prosthetic valve having a stent structure is disclosed in U.S. Pat. No. 5,957,949 to Leonhardt et al. entitled "Percutaneous Placement Valve Stent", which is incorporated by reference herein in its entirety.

Valvular heart disease is any disease process involving one or more of the valves of the heart, i.e., the aortic and mitral valves on the left and the pulmonary and tricuspid valves on the right. Severe valve damage may be treated with a valve replacement, with aortic valves and severely damaged mitral valves being the most often replaced heart valves. Some patients present with more than one heart valve being damaged so that the patient may need a dual valve replacement requiring more than one heart valve to be repaired or replaced. Whereas the use of minimally invasive techniques may be preferred, such an approach may be difficult in a dual valve replacement as placement of the prosthetic mitral valve prior to or subsequent of placement of the prosthetic aortic valve may be extremely difficult due to the relative locations of the two native valves, the lack of space in the left ventricle, and/or the concern of having to cross the first deployed prosthetic valve with the second delivery system and prosthetic valve under certain circumstances. Moreover, when a prosthetic valve is percutaneously delivered to replace a stenotic or insufficient aortic or mitral valve, a fundamental concern is that the prosthesis be deployed as precisely as possible so as to assure proper functioning, to avoid paravalvular leakage and to minimize any negative impact on the adjacent heart valve, each of which becomes more difficult to achieve with a dual valve replacement performed using multiple prosthetic valves and delivery devices. Further, sufficient prosthetic mitral valve fixation against high systolic pressures is also particularly important as migration or movement of the mitral valve prosthetic device can potentially block the left ventricular outflow tract or inhibit native or replacement aortic valve function. As such patients who must have a dual valve replacement most often undergo open heart surgical replacement procedures to implant the prosthetic aortic and mitral valves or one of the valves goes untreated. Accordingly a need exists in the art for apparatus and methods that allow a clinician to perform a dual heart valve replacement in a minimally invasive manner.

BRIEF SUMMARY OF THE INVENTION

Embodiments hereof are directed to a dual valve prosthesis having first and second prosthetic valve sections. The first prosthetic valve section includes a stent structure with a first prosthetic valve secured therein and the second prosthetic valve section includes an annular frame with a second prosthetic valve secured therein, wherein the annular frame extends from the stent structure such that the first and second prosthetic valves are laterally offset from each other when the dual valve prosthesis is in an expanded configuration. In an embodiment, the annular frame forms a border that radially extends around the second prosthetic valve to define an apposition surface and has a profile of a flat washer. In a method in accordance herewith, the first and second prosthetic valve sections include prosthetic aortic and mitral valves, respectively, and the dual heart valve prosthesis is configured to replace both the native aortic and mitral valves of the heart in a single transcatheter heart valve implantation procedure.

BRIEF DESCRIPTION OF DRAWINGS

The foregoing and other features and advantages of the invention will be apparent from the following description of embodiments thereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 2 is a sectional view of a distal portion of a delivery catheter with the dual valve prosthesis of FIG. 1 in a compressed delivery configuration therein.

FIGS. 3 and 4 illustrate a method of fabricating a stent structure and an annular frame of the dual valve prosthesis of FIG. 1 in accordance with an embodiment hereof.

DETAILED DESCRIPTION OF THE INVENTION

The following detailed description is merely exemplary in nature and is not intended to limit the invention or the application and uses of the invention. Although the description of embodiments hereof is in the context of concurrent aortic and mitral heart valve replacement, the invention may be adapted to be used for other concurrent valve replacement where it is deemed useful. Furthermore, there is no intention to be bound by any expressed or implied theory presented in the preceding technical field, background, brief summary or the following detailed description.

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician. Further the term "self-expanding" is used in the following description with reference to the stent structure and annular frame of the dual valve prosthesis and is intended to convey that the stent structure and annular frame are shaped or formed from a material that has a mechanical memory to return to an expanded deployed configuration from a compressed or constricted delivery configuration. Non-exhaustive exemplary materials that may be rendered self-expanding include stainless steel, a pseudo-elastic metal such as a nickel titanium alloy or nitinol, various polymers, and a so-called super alloy, which may have a base metal of nickel, cobalt, chromium, or other metal. Mechanical memory may be imparted to a wire or tubular structure used to form the stent structure and/or annular frame by thermal treatment to achieve a spring temper in stainless steel, for example, or to set a shape memory in a susceptible metal alloy, such as nitinol. Various polymers that can be made to have shape memory characteristics may also be suitable for use in embodiments hereof to include polymers such as polynorborene, trans-polyisoprene, styrene-butadiene, and polyurethane. As well poly L-D lactic copolymer, oligo caprylactone copolymer and poly cyclo-octine can be used separately or in conjunction with other shape memory polymers.

Figure 1:
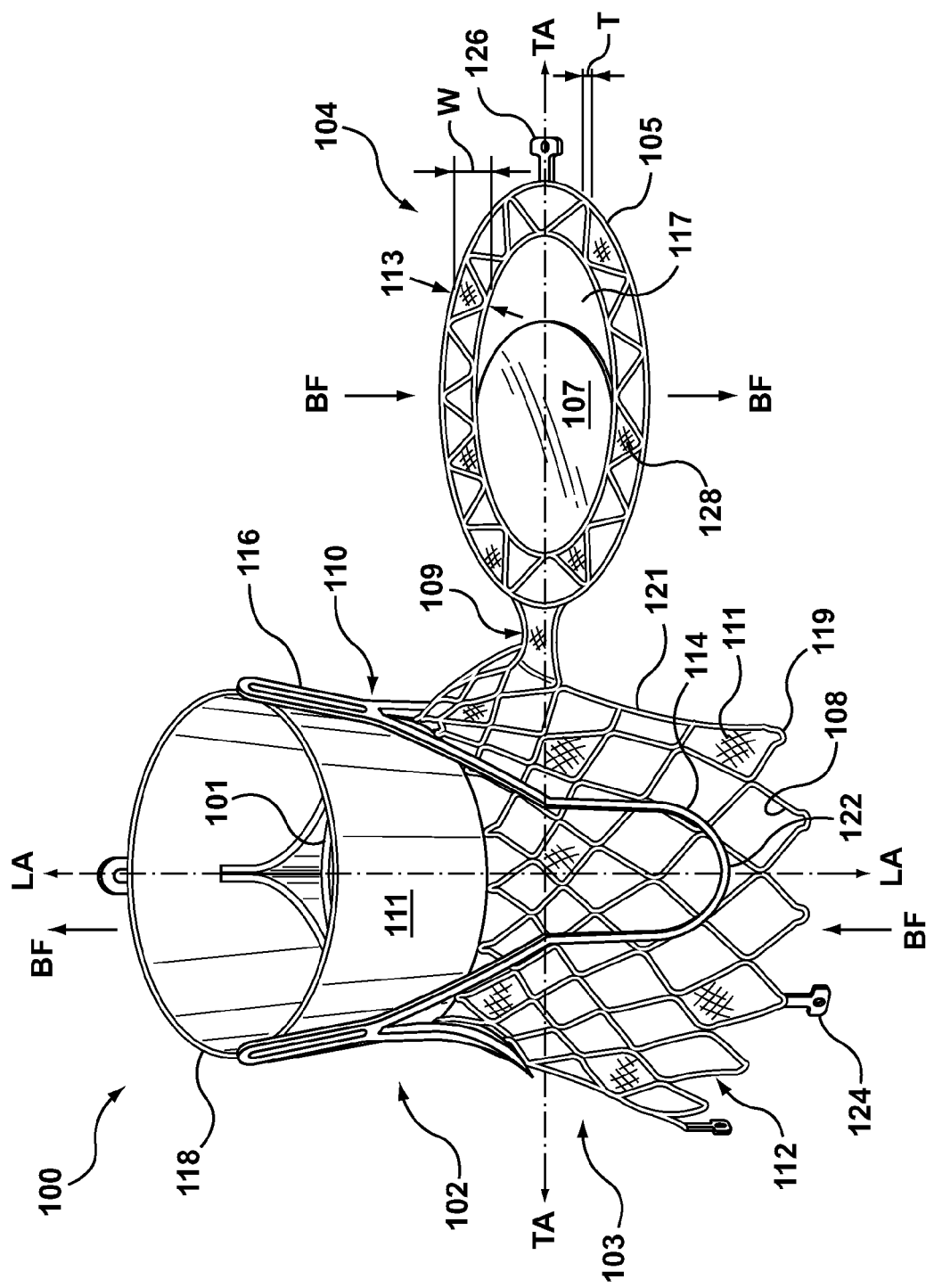
FIG. 1 is a perspective view of a dual valve prosthesis in an expanded configuration in accordance with an embodiment hereof.

Embodiments hereof are related to a dual valve prosthesis configured for deployment within the mitral and aortic valves of the heart in a single transcatheter heart valve implantation procedure. FIG. 1 is a perspective view of a dual valve prosthesis 100 in an expanded, deployed configuration in accordance with an embodiment hereof, with FIG. 2 being a sectional view of a distal portion of a delivery catheter 240 with dual valve prosthesis 100 in a compressed, delivery configuration therein. Dual valve prosthesis 100 includes a first prosthetic valve section 102 and a second prosthetic valve section 104. In an embodiment hereof, first prosthetic valve section 102 includes a first prosthetic valve 101 for replacing a native aortic valve and second prosthetic valve section 104 includes a second prosthetic valve 107 for replacing a native mitral valve.

First prosthetic valve section 102 includes a self-expanding stent structure 103 for anchoring dual valve prosthesis 100 within a beating heart. Stent structure 103 of first prosthetic valve section 102 includes a downstream or aortic portion 110 and an upstream or ventricular portion 112, wherein "upstream" and "downstream" are relative to a direction of blood flow when dual valve prosthesis 100 is properly implanted in vivo. Each of downstream and upstream portions 110, 112 of stent structure 103 is a collapsible, compressible structure made of a material having resiliency or shape memory characteristics in order to return first prosthetic valve section 102 to the deployed configuration shown in FIG. 1 upon release from a delivery device, such as delivery catheter 240. In an embodiment, downstream and upstream portions 110, 112 of stent structure 103 may be initially formed separately and then joined together by any means known to one of ordinary skill in the art such as, for instance, welding, gluing or suturing.

Stent structure upstream portion 112 is a patterned tubular device that defines substantially diamond shaped openings 108, although openings 108 may have any one of a variety of other shapes without departing from the scope hereof. Crimping eyelets 124 extend from upstream portion 112 at an upstream or inflow end 119 of first prosthetic valve section 102. Upstream portion 112 has a curved upstream edge defining an arched opening 121 when dual valve prosthesis 100 is in the expanded configuration that allows for the lateral positioning of second prosthetic valve section 104 relative to first prosthetic valve section 102. More particularly, a hinge segment 109 between upstream portion 112 of stent structure 103 and an annular frame 105 of second prosthetic valve section 104 extends from an area of an apex of arched opening 121 to laterally extend annular frame 105 therefrom when dual valve prosthesis 100 is in the expanded configuration as discussed in more detail below.

Stent structure downstream portion 110 includes three engagement arms 114 that are generally u-shaped and three prosthetic valve supports 116 to which leaflets of first prosthetic valve 101 are attached. Each engagement arm 114 extends upstream between respective prosthetic valve supports 116 to be positioned between upstream end 119 of first prosthetic valve section 102 and a downstream or outflow end 118 of first prosthetic valve section 102. Upstream ends 122 of engagement arms 114 may be described as being radially spaced or flared from the remainder of stent structure 103 and engagement arms 114 may be described as having a curved profile in the deployed/implanted configuration. When compressed for delivery within a sheath component of delivery catheter 240 as shown in FIG. 2, engagement arms 114 will somewhat straighten against upstream portion 112 of stent structure 103. When stent structure 103 is released from the sheath component, engagement arms 114 will return to their curved configuration with stent structure upstream portion 112 returning to its expanded configuration shown in FIG. 1. In an embodiment when first prosthetic valve section 102 is deployed to replace a native aortic valve, engagement arms 114 of downstream portion 110 engage the aortic sinuses and upstream portion 112 of stent structure 103 is deployed to seat within the annulus of the native aortic valve and to extend partially into the left ventricle, as discussed in more detail below.

In addition to stent structure 103, first prosthetic valve section 102 includes prosthetic valve 101 having three valve leaflets to form a tricuspid replacement valve. The valve leaflets of prosthetic valve 101 are sutured or otherwise securely and sealingly attached to the interior surface of stent structure 103 and/or graft material 111 that encloses or lines stent structure 103 as would be known to one of ordinary skill in the art of prosthetic valve construction. Prosthetic valve 101 is a one-way valve configured to collapse inwardly, i.e., towards a longitudinal axis LA of first prosthetic valve section 102, during diastole in order to inhibit retrograde blood flow and to open outwardly during systole to allow blood flow through first prosthetic valve section 102. In embodiments hereof, prosthetic valve 101 may be a bioprosthetic trileaflet heart valve, such as any one of the bioprosthetic trileaflet heart valves being used in implantable heart valve devices currently available that has been adapted for use herein.

Second prosthetic valve section 104 of dual valve prosthesis 100 includes self-expanding annular frame 105 that extends from stent structure 103. Annular frame 105 forms a circumferential border 113 of a width W that radially extends around the second prosthetic valve 107 to define an apposition surface thereabout. In an embodiment, width W may be in the range of 2.5 mm to 7.5 mm. Circumferential border 113 has triangular openings defined by the framework thereof, the triangular openings being shown by way of illustration and not limitation. One or both sides of circumferential border 113 may be covered with a graft material 128, such as any of the materials noted below for graft material 111, to aid in providing a seal against the native anatomy when second prosthetic valve section 104 is deployed within the heart. A crimping eyelet 126 extends from circumferential border 113 of annular frame 105. Annular frame 105 has a shape or a profile of a flat washer with a minimal thickness T that provides second prosthetic valve section 104 with a low ventricular profile that does not interfere with the left ventricular outflow tract. In an embodiment, thickness T may be in the range of 0.025 mm to 0.75 mm. Annular frame 105 so described aids in maintaining apposition of second prosthetic valve section 104 against then native anatomy to provide a seal there against. Second prosthetic valve 107 includes two valve leaflets to form a bicuspid replacement valve. The valve leaflets are sutured or otherwise securely and sealingly attached to an inner circumference of annular frame 105 to span a central opening 117 thereof.

When dual valve prosthesis 100 is in an expanded, deployed configuration, annular frame 105 laterally extends from upstream portion 112 of stent structure 103 such that first and second prosthetic valves 101, 107 are laterally offset from each other. In an embodiment, annular frame 105 is formed with upstream portion 112 of stent structure 103 as a single unit with an integral hinge segment 109 formed to extend therebetween. In such an embodiment, stent structure upstream portion 112 and annular frame 105 with integral hinge segment 109 may be formed by etching or otherwise cutting the patterns thereof from a tube, such as a tube 330 of nitinol, as shown in FIG. 3 and then performing a thermal treatment to shape set the structures in the expanded configuration shown in FIG. 4. When formed in this manner, hinge segment 109 is configured to return annular frame 105 to the shape set expanded configuration of FIG. 4 when dual valve prosthesis 100 is released from a compressed delivery configuration. In an embodiment, hinge segment 109 and annular frame 105 will rotate outwardly and upwardly relative to longitudinal axis LA of stent structure 103 when deployed from delivery catheter 240 within the heart to exert an apposition force AF against any heart structure in which annular frame 105 comes in contact. More particularly, when dual valve prosthesis 100 is deployed within the heart such that second prosthetic valve 107 secured within annular frame 105 is utilized as a replacement mitral valve, the apposition surface provided by circumferential border 113 of annular frame 105 exerts an apposition force against a surface of the left ventricle that surrounds the native mitral valve and is intended to seal against perivalvular leakage.

In another embodiment, annular frame 105 may be formed separately from upstream portion 112 of stent structure 103 with hinge segment 109 formed to integrally extend from annular frame 105 and then subsequently joined to upstream portion 112 or vice versa.

Figure 7:
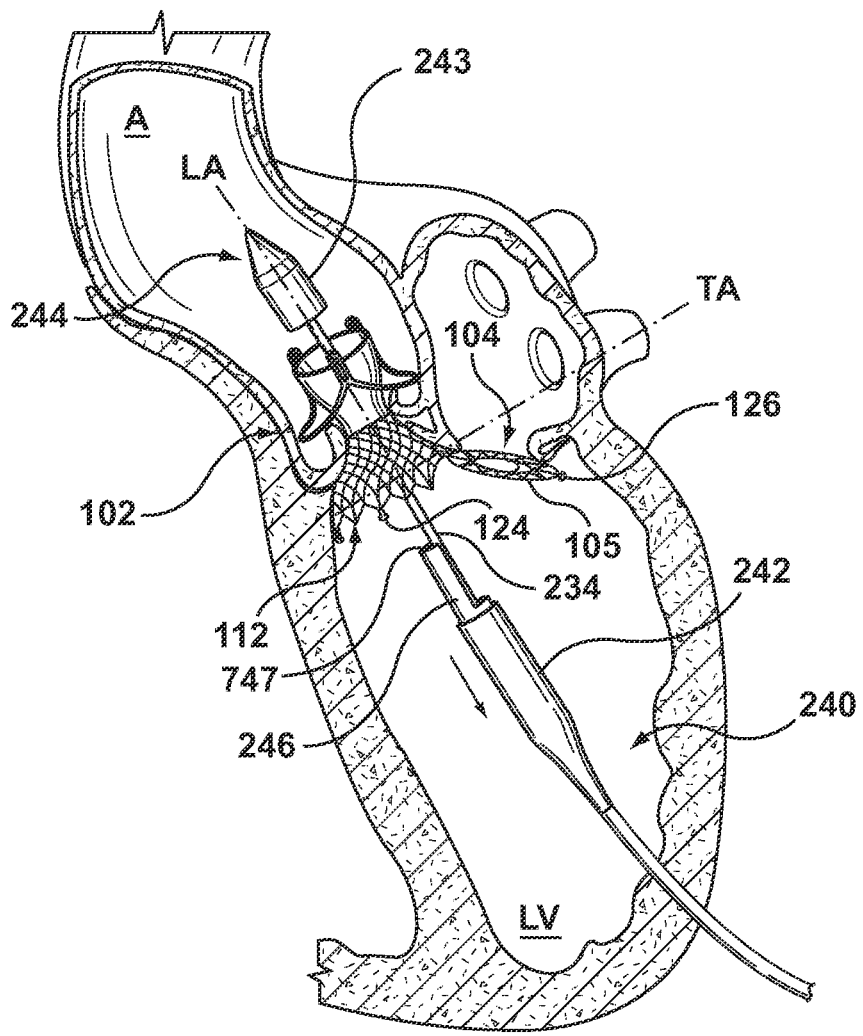

Depending on the anatomy of the heart in which dual valve prosthesis 100 is to be implanted and particularly in view of the anatomical position of the native aortic valve relative to the native mitral valve, in embodiments hereof second prosthetic valve section 104 in an expanded configuration may extend along an axis TA that is transverse to longitudinal axis LA of first prosthetic valve section 102, as shown in FIG. 1, may extend at an obtuse angle to longitudinal axis LA of first prosthetic valve section 102, as shown in FIG. 4, or may extend at an acute angle to longitudinal axis LA of first prosthetic valve section 102, as shown in FIG. 7. Accordingly in the expanded configuration annular frame 105 may laterally extend from stent structure 103 at an angle in the range of 45 to 135 degrees with respect to longitudinal axis LA of first prosthetic valve section 102, which is by way of example and not limitation as the actual angle may vary due to anatomical differences in the relative positions of the native valves. In each of the aforementioned expanded configurations when deployed within the heart, hinge segment 109 and annular frame 105 are configured or formed to rotate outwardly and upwardly relative to longitudinal axis LA of stent structure 103 to exert an apposition force AF against at least the heart structure that surrounds the native heart valve being replaced by second prosthetic valve 107.

Prosthetic valves 101, 107 secured within the interior of stent structure 103 and annular frame 105, respectively, are configured as one-way valves to allow blood flow in one direction and thereby regulate blood flow therethrough. In the embodiment shown and described with reference to FIG. 1, first prosthetic valve 101 includes three valve leaflets to form a tricuspid replacement valve and second prosthetic valve 107 includes two valve leaflets to form a bicuspid replacement valve or other leaflet structure that closes with pressure on the outflow and opens with pressure on the inflow. In other embodiments in accordance herewith, one or both of first and second prosthetic valves 101, 107 may be tricuspid or bicuspid replacement valves. In still other embodiments in accordance herewith, one or both of first and second prosthetic valves 101, 107 may be a single leaflet replacement valve or a replacement valve with more than three leaflets. Natural tissue for forming prosthetic valve leaflets for use in prosthetic valve sections in accordance with embodiments hereof may be obtained from, for example, heart valves, aortic roots, aortic walls, aortic leaflets, pericardial tissue, such as pericardial patches, bypass grafts, blood vessels, intestinal submucosal tissue, umbilical tissue and the like from humans or animals, such as tissue from bovine, equine or porcine origins. Synthetic materials suitable for use as prosthetic valve leaflets in embodiments hereof include DACRON® polyester commercially available from Invista North America S.A.R.L. of Wilmington, Del., polyurethane, Gore-Tex or other cloth materials, nylon blends, polymeric materials, and vacuum deposition nitinol fabricated materials. One polymeric material from which the replacement valve leaflets can be made is an ultra-high molecular weight polyethylene material commercially available under the trade designation DYNEEMA from Royal DSM of the Netherlands. With certain prosthetic leaflet materials, it may be desirable to coat one or both sides of the replacement valve leaflet with a material that will prevent or minimize overgrowth. It is further desirable that the prosthetic leaflet material is durable and not subject to stretching, deforming, or fatigue.

The valve leaflets of prosthetic valves 101, 107 are sutured or otherwise securely and sealingly attached to an interior surface of stent structure 103 and an inner circumference of annular frame 105 that defines central opening 117, respectively, and/or prosthetic valve 101 may be sutured or otherwise attached to graft material 111 that encloses or lines stent structures 103 as would be known to one of ordinary skill in the art of prosthetic valve construction. Graft material 111 may be a low-porosity woven fabric, such as polyester, Dacron fabric, or PTFE, which creates a one-way fluid passage when attached to the stent structure 103. In an embodiment, graft material 111 may be a knit or woven polyester, such as a polyester or PTFE knit, which can be utilized when it is desired to provide a medium for tissue ingrowth and the ability for the fabric to stretch to conform to a curved surface. Polyester velour fabrics may alternatively be used, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example. In another embodiment, graft material 111 may also be of a natural material such as pericardium or another membranous tissue such as intestinal submucosa.

The general direction of blood flow through dual valve prosthesis 100 when deployed in vivo is depicted by arrows BF in FIG. 1. In an embodiment in which dual valve prosthesis 100 is deployed within the heart, as described in more detail below, first prosthetic valve section 102 is a replacement aortic valve positioned to replace the native aortic valve and second prosthetic valve assembly 104 is a replacement mitral valve positioned to replace the native mitral valve with hinge segment 109 laterally extending therebetween to maintain the relative deployed positions of first and second prosthetic valve sections 102, 104. In certain methods of deploying dual valve prosthesis 100, one or both of hinge segment 109 and annular frame 105 may be deployed to secure the anterior leaflet of the native mitral valve to thereby prevent it from interfering with the operation of the replacement prosthetic aortic and/or mitral valves. In an embodiment, such methods may include advance preparation of the anterior leaflet of the mitral valve in order for subsequent deployment of dual valve prosthesis 100 to function to "catch" or secure the anterior leaflet in the open position and to avoid the mitral chordae.

Figure 6:
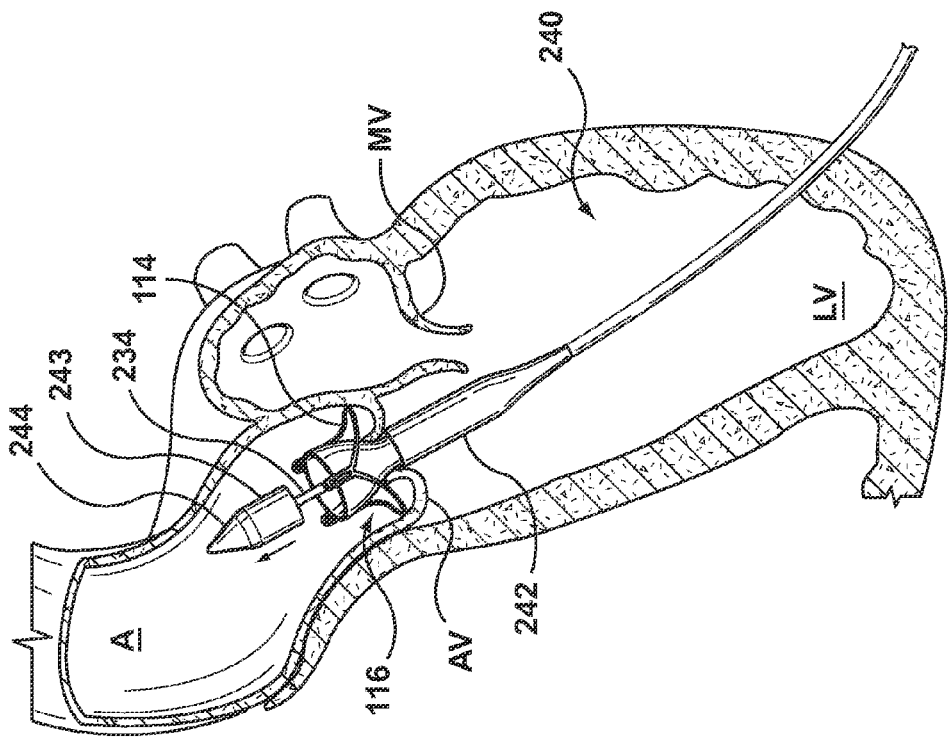
FIGS. 5-7 illustrate a method of performing a concurrent transcatheter valve replacement of the native aortic and mitral valves of a beating heart in accordance with an embodiment hereof.
Figure 5:
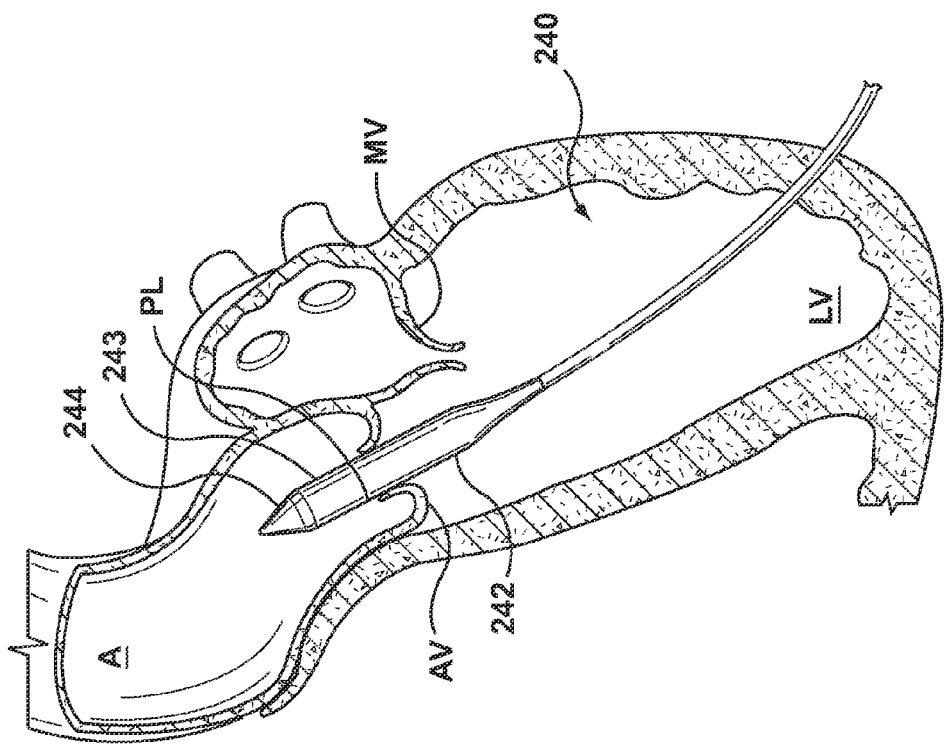

FIGS. 5-7 illustrate a method of performing a concurrent transcatheter valve replacement of the aortic valve and mitral valve of a beating heart in accordance with an embodiment hereof. Initially with reference to FIG. 2, delivery catheter 240 includes a distal tip 244 with a distal sheath section 243 that is attached to an inner shaft component 234, which extends within distal sheath section 243 and a proximal sheath section 242 to a proximal end (not shown) of delivery catheter 240 to be assessable by a clinician. Proximal and distal sheath sections 242, 243 may be collectively referred to herein as a sheath component that is attached at a proximal end thereof to an outer shaft component 236 that extends to the proximal end of delivery catheter 240 to be assessable by the clinician. In an embodiment hereof, distal tip 244 with distal sheath section 243 are configured to be releasably coupled to a distal end of proximal sheath section 242 at parting line PL. Dual valve prosthesis 100 is compressed in a delivery configuration within the sheath component with first and second prosthetic valve sections 102, 104 being sequentially loaded therein such that engagement arms 114 of stent structure downstream portion 110 of self-expanding stent structure 103 are held in a compressed state primarily by distal sheath section 243 and stent structure upstream portion 112 and annular frame 105 are held in a compressed state primarily by proximal sheath section 242.

In the embodiment shown in FIG. 2, a cylindrical rebated retainer 246 is sized to be slidably received within the sheath component and includes a tubular shaft component 248 that slidably extends between inner and outer shaft components 234, 236 to the proximal end of delivery catheter 240 to be assessable to the clinician. Rebated retainer 246 includes a cut-out 245 configured to accommodate second prosthetic valve section 104 in a collapsed, compressed state and a plurality of eyelet-shaped recesses 247 for receiving crimping eyelets 124, 126 of stent structure 103 and annular frame 105, respectively.

Delivery catheter 240 is shown in FIGS. 5-7 having been introduced into the left ventricle LV via a transapical minimally invasive procedure. In an embodiment, delivery catheter 240 so positioned may have been tracked through a trocar or other introducer device (not shown) that has been inserted through purse-string sutures (not shown) previously placed in the left ventricular apex. The purse-string sutures would be tightened around the trocar or other introducer device and a hemostasis valve would also be used to minimize blood leakage from the heart during the percutaneous replacement valve implantation procedure, as would be understood by one of ordinary skill in the art. As previously noted, the proximal ends (not shown) of delivery catheter 240 and its components extend out of the body to be accessible by a clinician.

Delivery catheter 240 is shown in FIG. 5 positioned through the native aortic valve AV such that distal tip 244 and distal sheath section 243 extend into the aorta A while proximal sheath section 242 is positioned to extend through the native aortic valve AV. In an embodiment, parting line PL between proximal and distal sheath sections 242, 243 is preferably positioned distal of the leaflets of the native aortic valve in line with the aortic sinuses. With reference to FIG. 6, distal tip 244 with distal sheath section 243 are distally advanced into the aorta relative to the remainder of delivery catheter 240 to release engagement arms 114 of stent structure 103 such that engagement arms 114 implant within the aortic sinuses. In an embodiment, delivery catheter 240 may be proximally retracted concurrent with the release of engagement arms 114, as shown in FIG. 6, to assure engagement arms 114 engage the aortic sinuses when deployed.

With reference to FIG. 7, proximal retraction of sheath component 240 relative to the remainder of delivery catheter 240 sequentially releases upstream portion 112 of stent structure 103 and then annular frame 105 to complete the deployment of dual valve prosthesis 100. More particularly when the proximal retraction of sheath component 240 uncovers a distal end 747 of rebated retainer 246, crimping eyelets 124 on upstream end 119 of first prosthetic valve section 102 are freed from corresponding recesses 247 in rebated retainer distal end 747 to thereby allow stent structure upstream portion 112 to return to its expanded configuration. In this manner, stent structure upstream portion 112 is implanted within the annulus of the native aortic valve and a portion of the left ventricle that surrounds the native aortic valve.

Continued proximal retraction of sheath component 240 uncovers crimping eyelet 126 on annular frame 105 to free eyelet 126 from its corresponding recess 247 in rebated retainer 246 and thereby releases annular frame 105 to return to its expanded configuration. The release of annular frame 105 from sheath component 242 permits annular frame 105 to rotate outwardly from stent structure 103 at hinge segment 109 until annular frame 105 is in apposition with a surface of the left ventricle that surrounds the native mitral valve. In this manner, the apposition surface of annular frame 105 of the second prosthetic heart valve section 104 exerts an apposition force that acts against the heart structure that surrounds the native mitral valve when deployed to implant second prosthetic valve section 104 against the native mitral valve and left ventricle. After implantation of dual valve prosthesis 100, delivery catheter 240 and its components are removed from the heart with the purse-string sutures noted above being tightened thereafter to close the opening in the left ventricular apex.

In an embodiment, deployment of stent structure upstream portion 112 and annular frame 105 is controlled by the clinician to occur when the heart is in diastole such that the anterior leaflet of the native mitral valve is captured and held against the ventricle wall by one or more of stent structure upstream portion 112, hinge segment 109 and annular frame 105 with the posterior leaflet of the native mitral valve being captured and held toward or against the ventricle wall by annular frame 105.

FIG. 7 depicts dual valve prosthesis 100 implanted within the heart with first prosthetic valve section 102 implanted to replace the native aortic valve and second prosthetic valve section 104 implanted to replace the native mitral valve. With a comparison of FIG. 1 and FIG. 7, prosthetic mitral valve 107 is a one-way bicuspid valve that is configured to be positioned in the heart within the left ventricle to permit blood flow through prosthetic mitral valve 107 in the direction of arrows BF during atrial emptying and ventricular filling when the leaflets of prosthetic mitral valve 107 open or part to allow blood to flow into the left ventricle. Prosthetic aortic valve 101 is a one-way tricuspid valve that is configured to be positioned in the heart between the left ventricle and the aorta within the annulus of the native aortic valve to permit blood flow through inflow end 119 of first prosthetic valve section 102 in the direction of arrows BF during systole when the leaflets of prosthetic aortic valve 101 open or part to allow blood to flow into the aorta. In embodiments hereof, each of prosthetic mitral valve 107 and prosthetic aortic valve 101 may be a bioprosthetic heart valve such as any one of the bioprosthetic heart valves being used in implantable heart valve devices currently available that has been adapted for use herein.

It will be appreciated by one of ordinary skill in the art that the stent structure of FIG. 1 is merely an exemplary stent structure and various other forms for stent structures that are suitable to anchor a replacement aortic valve within the native aortic valve may be adapted for use in embodiments hereof. For instance in one embodiment, stent structure 103 of first prosthetic valve section 102 may a patterned tubular device with a stepped outer diameter such that an aortic portion of the stent structure has an expanded diameter that is greater than an expanded diameter of a ventricular portion of the stent structure. The aortic portion of the stent structure would be sized to be expandable within the aortic sinuses for securing first prosthetic valve section 102 with respect to the native aortic valve without the use of engagement arms 114. Further as would be appreciated by one of ordinary skill in the art, various methods of fabrication can be used in accordance with embodiments hereof to manufacture self-expanding stent structure 103 and annular frame 105 as either an integral unitary structure, such as by laser cutting or chemical etching the patterns thereof in a flat sheet or a tube, or a plurality of individual structures that are joined, such as by one of welding, soldering, or the like, without departing from the scope of the present invention. Further in other embodiments in accordance herewith, stent structure 103 and annular frame 105 may be made balloon-expandable or one may be self-expandable with the other balloon-expandable.

While various embodiments have been described above, it should be understood that they have been presented only as illustrations and examples of the present invention, and not by way of limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A dual valve prosthesis comprising:
    a first prosthetic valve section having a stent structure with a first prosthetic valve secured therein; and
    a second prosthetic valve section having an annular frame with a second prosthetic valve secured therein, wherein the annular frame has a profile of a flat washer and is attached to the stent structure by a hinge segment, wherein when the dual valve prosthesis is in an expanded configuration the annular frame laterally extends from the stent structure with the hinge segment there between such that the first and second prosthetic valves are laterally offset from each other by the hinge segment.

2. The dual valve prosthesis of claim 1, wherein the annular frame forms a border that radially extends around the second prosthetic valve to define an apposition surface.

3. The dual valve prosthesis of claim 1, wherein the hinge segment and the annular frame extend from an arched opening defined by an upstream edge of the stent structure.

4. The dual valve prosthesis of claim 3, wherein at least an upstream portion of the stent structure, annular frame and hinge segment are an integral self-expanding structure with a shape set to return to the expanded configuration from a compressed delivery configuration.

5. The dual valve prosthesis of claim 4, wherein a downstream portion of the stent structure includes a plurality of engagement arms each having an upstream end that is radially spaced from the upstream portion of the stent structure.

6. The dual valve prosthesis of claim 1, wherein the first prosthetic valve is a trileaflet prosthetic aortic valve.

7. The dual valve prosthesis of claim 6, wherein the second prosthetic valve is a bicuspid prosthetic mitral valve.

8. The dual valve prosthesis of claim 1, wherein in the expanded configuration the annular frame laterally extends from the stent structure at an angle in the range of 45 to 135 degrees with respect to a longitudinal axis of the first prosthetic valve section.

9. A dual heart valve prosthesis comprising:
    a first prosthetic valve section including a stent structure with a first prosthetic heart valve secured therein; and
    a second prosthetic valve section including an annular frame with a second prosthetic heart valve secured therein, the annular frame having a central opening within which the second prosthetic heart valve is secured,
    wherein when the dual heart valve prosthesis is in an expanded configuration the annular frame forms a circumferential border around the second prosthetic heart valve that extends in a radially outward direction from the central opening of the annular frame with a width that is greater than an overall thickness of the annular frame, and wherein when the dual heart valve prosthesis is in the expanded configuration the first and second prosthetic valve sections are laterally offset from each other by a hinge segment that extends between the stent structure of the first prosthetic valve section and the annular frame of the second prosthetic valve section.

10. The dual heart valve prosthesis of claim 9, wherein the width of the circumferential border extends between an outer circumference of the annular frame and an inner circumference of the annular frame which is defined by the central opening.

11. The dual heart valve prosthesis of claim 10, wherein the circumferential border defines a flat apposition surface on a first side thereof.

12. The dual heart valve prosthesis of claim 9, wherein the annular frame has a profile of a flat washer.

13. The dual heart valve prosthesis of claim 9, wherein the first prosthetic heart valve is a prosthetic aortic valve.

14. The dual heart valve prosthesis of claim 13, wherein the second prosthetic heart valve is a prosthetic mitral valve.

15. The dual heart valve prosthesis of claim 9, wherein in the expanded configuration the annular frame laterally extends from the stent structure at an angle in the range of 45 to 135 degrees with respect to a longitudinal axis of the first prosthetic valve section.

16. The dual heart valve prosthesis of claim 9, wherein the width of the circumferential border formed by the annular frame is in the range of 2.5 mm to 7.5 mm and wherein the thickness of the annular frame is in the range of 0.025 mm to 0.75mm.

* * * * *